United States Patent
Mollemans et al.

(10) Patent No.: US 8,824,764 B2
(45) Date of Patent: Sep. 2, 2014

(54) METHOD FOR DIGITIZING DENTO-MAXILLOFACIAL OBJECTS

(75) Inventors: Wouter Mollemans, Antwerp (BE); Veerle Wouters, Kessel-lo (BE); Filip Schutyser, Sint-Niklaas (BE)

(73) Assignee: Medicim N.V., Mechelen (BE)

( * ) Notice: Subject to any disclaimer, the term of this patent is extended or adjusted under 35 U.S.C. 154(b) by 192 days.

(21) Appl. No.: 13/394,269

(22) PCT Filed: Sep. 1, 2010

(86) PCT No.: PCT/EP2010/005355
§ 371 (c)(1), (2), (4) Date: Apr. 18, 2012

(87) PCT Pub. No.: WO2011/026609
PCT Pub. Date: Mar. 10, 2011

(65) Prior Publication Data
US 2012/0201443 A1     Aug. 9, 2012

(30) Foreign Application Priority Data

Sep. 4, 2009  (EP) .................................. 09169487

(51) Int. Cl.
- *G06K 9/00* (2006.01)
- *G06T 7/00* (2006.01)
- *A61C 9/00* (2006.01)
- *A61C 11/00* (2006.01)
- *A61C 5/00* (2006.01)

(52) U.S. Cl.
CPC ............ *G06T 7/0081* (2013.01); *G06T 7/0091* (2013.01); *A61C 9/0046* (2013.01); *G06T 2207/20041* (2013.01); *G06T 2207/30036* (2013.01); *G06T 2207/10081* (2013.01); *G06T 2207/20144* (2013.01); *G06T 2207/20148* (2013.01)
USPC ........................... 382/131; 433/213; 433/215

(58) Field of Classification Search
USPC ......... 382/128, 129, 130, 131, 132, 133, 134, 382/164, 171, 173; 433/24, 75, 172, 173, 433/213, 214, 223, 26; 623/901, 914
See application file for complete search history.

(56) References Cited

U.S. PATENT DOCUMENTS

| | | | |
|---|---|---|---|
| 4,663,720 | A | 5/1987 | Duret et al. |
| 5,360,446 | A | 11/1994 | Kennedy |

(Continued)

FOREIGN PATENT DOCUMENTS

| | | |
|---|---|---|
| EP | 1624411 A2 | 2/2006 |
| EP | 1649811 A1 | 4/2006 |

(Continued)

OTHER PUBLICATIONS

Eggers et al., "Geometric accuracy of digital volume tomography and conventional computed tomography", British Journal of Oral and Maxillofacial Surgery, vol. 46, No. 8, Dec. 2008, pp. 639-644.

Maes et al., "Multimodality Image Registration by Maximization of Mutual Information", IEEE Trans. on Medical Imaging, 16(2):187-198, Apr. 1997.

(Continued)

*Primary Examiner* — Abolfazl Tabatabai
(74) *Attorney, Agent, or Firm* — Knobbe, Martens, Olson & Bear LLP

(57) ABSTRACT

A method for capturing the shape of a dento-maxillofacial object out of volumetric image data of the dento-maxillofacial object is described. The method includes performing a segmentation of the volumetric image data with at least one calculated segmentation parameter indicative of the distinction between the dento-maxillofacial object and its background and derived from a calibration procedure. The method further includes capturing the shape of the dento-maxillofacial object from the segmented volumetric image data.

23 Claims, 3 Drawing Sheets

(56) References Cited

U.S. PATENT DOCUMENTS

| | | | |
|---|---|---|---|
| 5,725,376 | A | 3/1998 | Poirier |
| 5,768,134 | A | 6/1998 | Swaelens et al. |
| 5,816,810 | A | 10/1998 | Antonson et al. |
| 5,851,115 | A * | 12/1998 | Carlsson et al. .............. 433/215 |
| 5,857,853 | A | 1/1999 | Van Nifterick et al. |
| 6,319,006 | B1 * | 11/2001 | Scherer et al. ................ 433/215 |
| 7,123,767 | B2 | 10/2006 | Jones et al. |
| 7,331,786 | B2 | 2/2008 | Poirier |
| 2002/0028418 | A1* | 3/2002 | Farag et al. ..................... 433/29 |
| 2005/0019732 | A1 | 1/2005 | Kaufmann |
| 2008/0159608 | A1 | 7/2008 | Suetens et al. |
| 2011/0059413 | A1 | 3/2011 | Schutyser et al. |

FOREIGN PATENT DOCUMENTS

| | | |
|---|---|---|
| EP | 1808129 A1 | 7/2007 |
| GB | 2440267 A | 1/2008 |
| JP | 2008-253808 A | 10/2008 |
| WO | WO 00/19929 | 4/2000 |
| WO | WO 2007/046024 | 4/2007 |

OTHER PUBLICATIONS

Arun et al., "Least Squares fitting of Two 3-D Point Sets", IEEE Trans. Pattern Analysis and Machine Intelligence, 9(5), Sep. 1987, pp. 698-700.

Pratik Ghosh et al., "Pure Phase-Encoded MRI and Classification of Solids", IEEE Transactions on Medical Imaging, IEEE Service Center, Piscataway, NJ, US, vol. 14, No. 3, Sep. 1, 1995, pp. 616-620.

Lorensen, et al., "Marching Cubes: A High Resolutions 3D Surface Construction Algorithm", Computer Graphics, vol. 21, No. 4, pp. 163-169, Jul. 1987.

International Search Report for PCT/EP2010/005355 dated Dec. 6, 2010.

International Preliminary Report on Patentability for PCT/EP2010/005355 dated Mar. 6, 2012.

State Intellectual Property Office of People's Republic of China, First Office Action, dated Mar. 4, 2014, for Application No. 201080038917.0.

Zhang, Lin et al., Study on Three Dimensional Virtual Surgical Craniofacial Surgery Simulation, Journal of Wenzhou Medical College, Jun. 2004, pp. 176-178.

* cited by examiner (a) (b)

(a) (b)

(a) (b)

METHOD FOR DIGITIZING DENTO-MAXILLOFACIAL OBJECTS

CROSS-REFERENCE TO RELATED APPLICATIONS

This application is a national stage application under 35 U.S.C. §371 of PCT Application No. PCT/EP2010/005355, filed on Sep. 1, 2010, which published in English as WO 2011/026609 on Mar. 10, 2011 and which claims priority benefit of European Patent Application No. 09169487.7, filed on Sep. 4, 2009, the entire contents of which applications and publication are herein incorporated by reference in their entirety.

BACKGROUND

1. Field of the Invention

The present invention relates to a system and method for capturing the shape of a dento-maxillofacial object out of volumetric image data of that object. Further, the present invention relates to a system and method for determining a parameter for use in digitizing the dento-maxillofacial object.

2. Description of the Related Technology

Dento-maxillofacial treatments are related to the dentition, the skull and the facial soft tissues. The scope of the treatments goes from handling teeth—such as aligning, restoring crowns, extracting, restoring including root and crown—over bone related treatments—such as maxillofacial surgery involving surgical remodelling or restoring of the skull and dentition, encompassing surgical interventions of repair, in particular, of a mis-positioning of the jaws with respect to one another, called orthognathic surgery, temporomandibular joint (TMJ) treatments—over facial soft tissue treatments—such as tissue sculpting, lifting, and so forth. Important in these treatments is creating a good occlusion and smile line. With 'occlusion' is meant the manner in which the teeth from the upper and lower arches come together when the mouth is closed.

Since dento-maxillofacial treatments are complex and have a big impact on the patient's facial outlook, accurate treatment planning is required. Computer aided dento-maxillofacial planning systems are becoming available which digitize the traditional manual treatment planning process. In order to be able to optimize the treatment plan, it is often necessary to incorporate in these systems a digitized version of dento-maxillofacial objects, such as dental impressions, dental stone models or removable prostheses, etc. Consequently, a need exists in some cases to enable accurate digitization of dento-maxillofacial objects.

Dento-maxillofacial objects are characterized by a highly irregular shape showing various undercuts and small details. This characteristic makes digitizing the shape a challenging task.

To digitize dento-maxillofacial objects, surface scanning based on stereo-imaging, structure light imaging, laser scanning or, amongst others, conoscopic holography can be applied. These methods can provide highly detailed surface scans of the objects. Although some techniques are more flexible with respect to the variety of shapes they can scan, certain shapes remain difficult to digitize.

An alternative method to digitize the shape of the dento-maxillofacial material is using volumetric imaging techniques, such as destructive scanning or tomographic imaging. Tomographic imaging includes all image modalities that generate tomographic images. These tomographic images can be arranged in a 3D image volume.

An example of such tomographic imaging is computed tomography (CT) scanning. With this modality, X-rays are employed to digitize the shape of the dento-maxillofacial material. This is typically done in an industrialized environment based on industrial CT scanners or micro-CT scanners. However, this approach needs a significant investment and creates a logistic hassle. For example, a dental impression deforms when it dries. Therefore, it is advisable to digitize the impression as soon as possible and to carefully control the environment in which it is stored.

Although various imaging techniques exist for scanning objects, the problem remains that capturing the exact contour or the shape of the objects out of the volumetric image data is very difficult or inaccurate. Moreover, this contouring or shaping is usually performed in a subjective manner. This contouring process is often also called segmentation of the volumetric image data.

Consequently, there is a need in some cases for an accurate method to capture the shape out of volumetric image data, such as the shape of dento-maxillofacial materials in a more reliable way.

In WO00/19929 the volume imaging technique is described of destructive scanning, whereby images of slices are taken.

Document U.S. Pat. No. 7,123,767 describes techniques for segmenting a digital dentition model into models of individual components using e.g., CT scans. Several 3D segmentation techniques are described, many of which are human-assisted. Other computer-implemented techniques have a drawback that only interproximal margins are created, instead of an accurate threshold value. This document is however not concerned with the accuracy of the segmentation of a digital dentition model, even though this is a crucial factor.

There is also a need in some cases to offer dental professionals the possibility to scan dento-maxillofacial materials with volume imaging techniques, such as tomographic imaging, that are easily accessible or installed in the dental office. An example of such a tomographic imaging method is CT scanning with a standard medical CT scanner or a Cone-Beam CT scanner.

Tomographic imaging creates a volumetric image dataset, or even several ones, out of which the surface of the dento-maxillofacial object needs to be segmented. Given the large variety of tomographic imaging equipment, an easy and highly automated method may be required in order to allow convenient, accurate digitization of the shape of dento-maxillofacial objects.

The paper '*Geometric accuracy of digital volume tomography and conventional computed tomography*' (Eggers et al., British Journal of Oral and Maxillofacial Surgery, vol. 46, no. 8, December 2008, pp. 639-644) is concerned with the question whether digital volume tomographic imaging is suitable for image-guided operating. The geometric accuracy is important for accurate patient to image registration, and so for the safety of patients, digital volume tomography is found to be an appropriate method.

European patent application EP1808129 discloses a human body information extraction device for extracting human body information including position information from a reference position, from 3D information on the human body elements obtained from a CT information or the like in which the position information from the reference position with respect to a human body element is unknown. In the proposed solution a reference plane for positioning is detected by detecting information on a common positioning member contained in both of the 3D human body information from the CT information and a 3D model information from a human body model.

SUMMARY

A system and method are provided for generating a digital model of the shape of a dento-maxillofacial object out of a volumetric image data set, whereby the drawbacks and limitations of the prior art are overcome.

In one aspect there is a method for capturing the shape of a dento-maxillofacial object out of volumetric image data of the dento-maxillofacial object. The method comprises the steps of performing a segmentation of the volumetric image data with at least one calculated segmentation parameter indicative of the distinction between the dento-maxillofacial object and its background, and capturing the shape of the dento-maxillofacial object from the segmented volumetric image data.

State-of-the-art methods rely on the intuitive segmentation by the user of the system to obtain a digitization of the material. However, this subjective method implies a big risk related to the correctness of the shape. In a solution according to the system and method, this issue can be automatically solved, while keeping the requirement of using readily available equipment to the clinician or dentist, such as a CT scanner.

In another aspect there is a method for determining (e.g., calculating) at least one segmentation parameter of volumetric image data of a dento-maxillofacial object, whereby the method comprises the steps of obtaining volumetric image data of a calibration object with the same imaging protocol as used for obtaining the volumetric image data of the dento-maxillofacial object, and determining the at least one segmentation parameter by means of the shape of the calibration object and the volumetric image data of the calibration object. In the method the at least one segmentation parameter is determined by aligning image data sets of the calibration object and of the volumetric image data of the calibration object, deriving a measure for comparing the aligned data sets, and deriving the at least one segmentation parameter based on a selection criterion on the measure.

In one embodiment the method may comprise the step of computing an accuracy measure of the segmentation obtained by applying the at least one segmentation parameter.

In a specific embodiment the alignment can be performed by voxel-based registration or by a point based alignment method.

In another specific embodiment the selection criterion may be based on a histogram that is built by measuring the image values in the volumetric image data of the calibration object at the surface of the aligned calibration object.

In an embodiment the volumetric image data may be obtained by a tomographic imaging technique comprising CT scanning.

In an embodiment the calibration object may have material properties substantially equal to those of the dento-maxillofacial object for a specific imaging technique. In another embodiment the calibration object may have shape characteristics substantially equal to the shape of the dento-maxillofacial object. In a further embodiment the calibration object may have dimensions substantially equal to the dimensions of the dento-maxillofacial object.

In another aspect there is a method for digitizing a dento-maxillofacial object comprising of the steps of[:] a) taking a calibration object designed with material properties suitable for a tomographic imaging technique; and optionally substantially equal to the dento-maxillofacial object in both shape and dimensions; b) scanning the calibration object with a tomographic imaging device; c) deriving at least one segmentation parameter; d) scanning the dento-maxillofacial object with the same imaging device and settings as used for the calibration object in step b; and e) applying a segmentation on the scanned dento-maxillofacial object with the at least one segmentation parameter obtained from step c.

In an embodiment, the segmentation of the method may be thresholding.

In yet another aspect the method can be related to a program, executable on a programmable device containing instructions, which when executed, perform the method as in any of the methods as described above.

In a further aspect there is a kit comprising a calibration object and a data carrier containing the program as described above. In one embodiment the kit further may comprise a carrier object for positioning the calibration object in an imaging device, the carrier object imaging may be significantly different than the calibration object.

In another aspect there is a method for designing a calibration object.

An advantage of the method can be to correctly, robustly and reliably digitize a material with the equipment readily available to clinicians or dentists. The method guarantees that a detailed and accurate surface can be automatically generated given the resolution of the volumetric image volume acquired by the tomographic imaging method.

DETAILED DESCRIPTION OF CERTAIN EMBODIMENTS

The term "volumetric scan" can mean data obtained by a volume imaging technique such as tomographic imaging or destructive scanning. Synonyms used throughout the text can be "volumetric image data" or "volumetric image dataset".

For further storage, processing, design and production of various products in the medical field, accurate digitization of a material reflecting a shape of the body may need to be performed. Since this shape can be highly irregular, imaging the entire shape in one fast acquisition can be difficult.

In the dento-maxillofacial field, various objects can be used for this purpose. One family of materials can be impression materials. Impressions can be made of anatomical parts such as teeth, face, ears. Another family of materials may be plaster casts. Plaster models of various anatomical models can be typically produced from impressions. Yet other materials, such as prostheses, or especially designed materials, such as radiographic guides and wax-ups, may need to be digitized.

To digitize dento-maxillofacial objects a volumetric imaging technique, such as destructive imaging or tomographic imaging, may be used. In another embodiment surface scanning techniques can be applied.

A typical tomographic scanning technique can use X-rays. In a clinical or dental environment, scanning with a CT scanner can be used for digitizing the patient's anatomy. The CT scanner can be a medical CT scanner, a cone-beam CT scanner (CBCT) or micro CT scanner (µCT).

The dento-maxillofacial object reflecting a shape of the body can be positioned on a carrier material that images very differently. When the material properties of these two materials are different, the object reflecting a shape of the body can be clearly seen. When the material is scanned, it may show as if it is floating. For imaging using X-rays, very radio-lucent carrier material can be good, such as a sponge. However, for the segmentation of the exact shape out of this volumetric scan, given the broad range of equipment present in the medical and dental field, a new step may be required, which suits the medical or dental working environment. For this purpose a calibration and segmentation procedure is provided.

Figure 1:
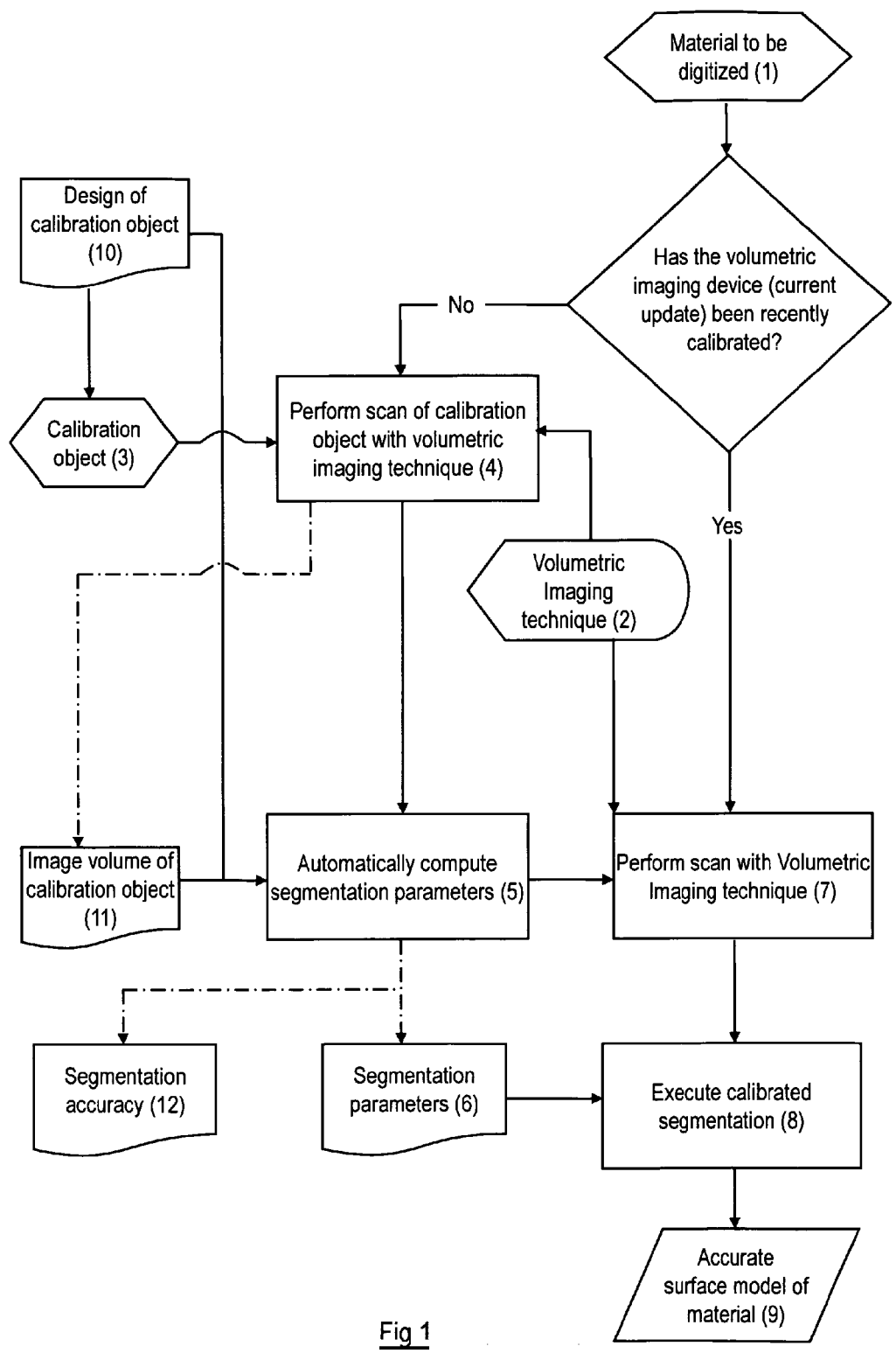
FIG. 1 is a workflow diagram of an example digitizing method.

FIG. 1 represents a workflow of a method for digitizing an object.

In one embodiment a tomographic scanner (2) can be calibrated by performing a scan (4) of a calibration object (3). From this scan one or more segmentation parameters (6) can be automatically computed (5). The calibration object (3) can be specifically designed (10) for the object to be digitized (1) with the calibrated tomographic scanner (7). A calibrated segmentation (8) can be performed on the scanned material to provide an accurate surface model (9) of said material.

A calibration object (3) can be designed. The material for the calibration object may have similar material properties for the tomographic imaging method as the target material that needs to be digitized. The exact shape information (10), which can be similar to the shape of the real material that needs to be digitized, is known by design.

The calibration object can be scanned (4) in the same way and with the same scanner as the target material is scanned. Based on the volumetric image data from the scan (11) and the known shape from the design (10), the parameters that generate the exact shape for a specific segmentation approach (6) can be determined (5). With these parameters, the binary decision point where the exact shape of the scanned object can be located is determined. In addition to this, an accuracy measure of the resulting segmentation can be computed (12).

Now, the actual material can be scanned with the same scan protocol as the calibration scan (7). The segmentation algorithm can be applied (8) with the determined parameters (6). In this way the exact shape of the material may be obtained (9).

The calibration scan can easily be redone with a regular frequency in time, or when changes or updates to the CT-scanning equipment, or to the materials used, occur. This method may be fast and can be handled by the clinicians and their team themselves.

In a specific embodiment segmentation of a surface out of a volumetric image volume can be performed by thresholding. A threshold value can define the transition between the material and background, and hence the surface of the material.

Figure 2:
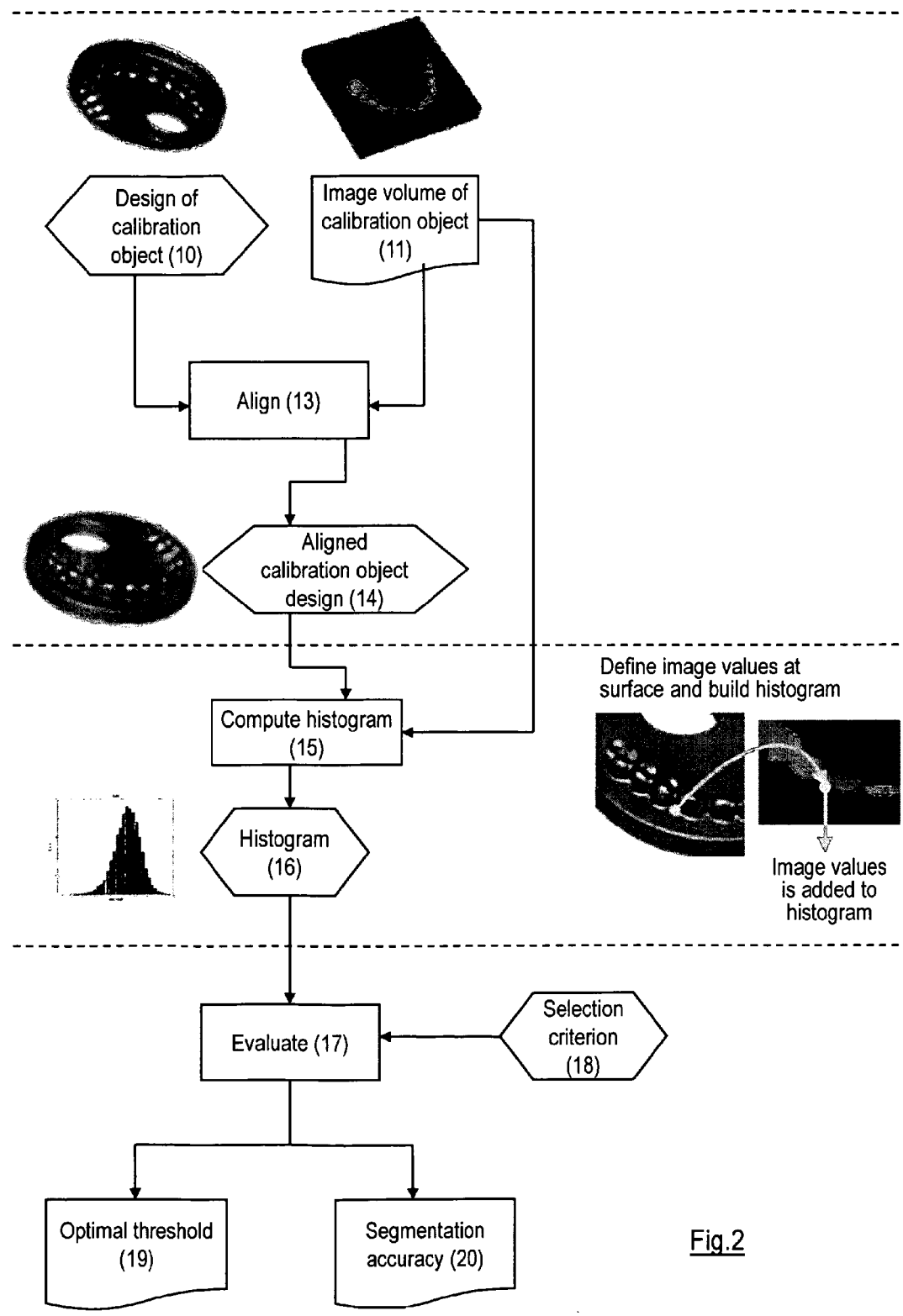
FIG. 2 is a flow diagram of an outline of an example algorithm for defining the optimal threshold value.

FIG. 2 illustrates an example algorithm for automatically computing the optimal threshold value or segmentation parameters (5). The method can be related to a computer program, executable on a programmable device containing instructions, which when executed, perform the algorithm. The computer program may be storeable on a computer readable medium, and may be executed by a computer, such as a personal computer, which may be connected to a network.

The algorithm may require two input data sets: the calibration object design (10) and the image volume(s) of the calibration object (11). The algorithm can comprise as major steps: aligning the two input data sets (13-14), deriving a measure for comparing the aligned data sets (for example, by building a histogram (15-16)) and finally deriving the value of the segmentation parameter, e.g., the optimal threshold value (17-20).

Since the calibration object design (10) and the image volume (11) may not be aligned an alignment step is required. Aligning can be defined as searching a transformation so that the transformed object and the image volume share the same 3D space, and thus coincide. To obtain this alignment different procedures can be used. A possible approach is as follows. First, an image volume based on the calibration object design (10) can be computed. Next this image volume data can be aligned with the image volume data of the calibration object obtained through tomographic imaging (11). The outcome of this algorithm can be a transformation which can then be applied to the calibration object design (10) to obtain an aligned calibration object design (14). The aligned calibration object design (14) may coincide with the image volume of the calibration object (11) in the same 3D space.

In one embodiment the alignment can be done by voxel-based registration based on maximization of mutual information ('*Multimodality image registration by maximization of mutual information*', Maes et al., IEEE Trans. Medical Imaging, 16(2):187-198, April 1997). In another embodiment a point based alignment method ('*Least square fitting of Two 3D Point Sets*', Arun et al., IEEE Trans. Pattern Analysis and Machine Intelligence, 9(5), September 1987) can be used. This point based alignment method may first extract well definable points or features on the calibration object design (10) and in the image volume of the calibration object (11). Next the method may search the transformation which aligns the corresponding 3D points of both data sets.

In a second step, the algorithm may measure the image values in the image volume of the calibration object (11) at the surface of the aligned calibration object design (14). All measured image values can be stored and a histogram of the stored image values (15) may be built. To improve the stability of the algorithm the measure area can be extended towards a small region around the surface of the aligned calibration object design (14). In this way noise in the alignment algorithm or in the scanned data can be partially eliminated.

At last the optimal threshold value (19), in other words the segmentation parameter, can be derived (17) by using a selection criterion (18) in combination with the generated image values histogram (16). Possible selection criteria (18) can be: mean image value, most frequent image value, maximum image value, etc. Different selection criteria may result in slightly different threshold values and the optimal selection criterion can be dependent on the final application.

After defining an optimal threshold value a measure of the to-be-expected overall accuracy (20) of the segmentation can be obtained. To calculate this value a surface representation can be generated out of the scanned image volume of the calibration object (11) using a marching cubes algorithm (Proc. of SIGGRAPH, pp. 163-169, 1987) and the derived optimal threshold value. Next a distance map between this surface representation and the calibration object design (10) can be calculated. This distance map or any statistical derived measure from this distance map can represent the to-be-expected accuracy of the overall digitization procedure for the material to be digitized given the tomographic imaging method and equipment with the according imaging protocol.

An alternative method for automatically computing the optimal threshold value can comprise the steps of aligning the scanned calibration object and the virtual calibration object design, generating for any threshold value a distance map between the reconstructed surface of the scanned object and the virtual surface of the object design and deriving the optimal threshold value based on the calculated distance maps.

Example 1

Design of Calibration Object (10) for Acrylic Prosthesis

In case the material to be digitized (1) is an acrylic dental prosthesis, some specific guidelines can be considered when designing the calibration object (10). First, the volume of the designed object can be more or less equal to the volume of a typical dental prosthesis. Moreover it can be preferred that the surface of the object contains sufficient detailed 3D information, e.g., shape variation, so that the accuracy of the algorithm can be guaranteed. Finally the properties of the material used for the calibration object can be similar or equal to those of the material to be digitized for the specific tomographic imaging technique.

Figure 3:
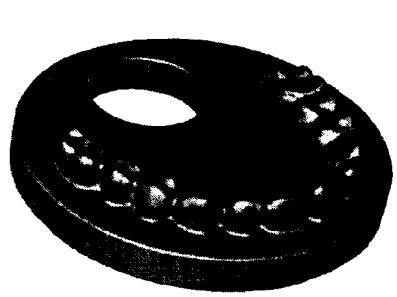
FIG. 3 is a diagram of an example calibration object design as scan (a) and produced in polycarbonate (b)
Figure 3:
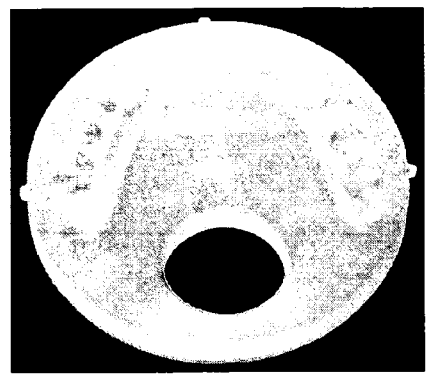

In case the tomographic imaging method is CT scanning for the acrylic prosthesis, the calibration object (10) can be designed as follows. The calibration object can consist of a typical dental surface virtually mounted on a cylinder with a small height. The designed object can be produced in polycarbonate which has similar radio-opacity characteristics as the acrylic materials used for producing dental prostheses (FIG. 3). An example of such polycarbonate is TECANAT™.

Example 2

Design of Calibration Object (10) for a Dental Impression

In case the material to be digitized is a dental impression and the tomographic imaging method is CT scanning, some specific guidelines can be considered when designing the calibration object (10). First, it should be noted that many dental impression materials exist. All these materials can have different radio-opacity characteristics. Therefore the designed calibration object can be usable for any of these dental impression materials. Second, it can be preferred that the volume of the calibration object may be more or less equal to the volume of a typical dental impression. Finally the calibration object can include sufficient detailed 3D information, e.g., shape variation, so that the accuracy of the algorithm can be guaranteed. To meet these guidelines a calibration object can be produced and a special calibration procedure can be elaborated.

Figure 4:
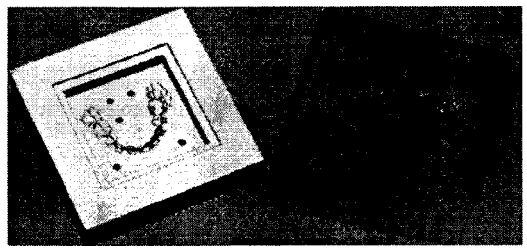
FIG. 4 is a diagram of examples of (a) the calibration object having a container part and a top part; and (b) the positioning of the top part on the container part.
Figure 4:
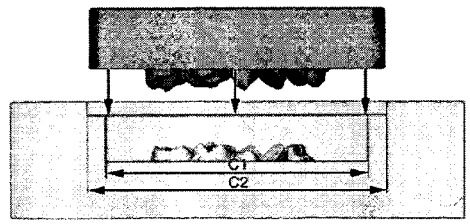
Figure 5:
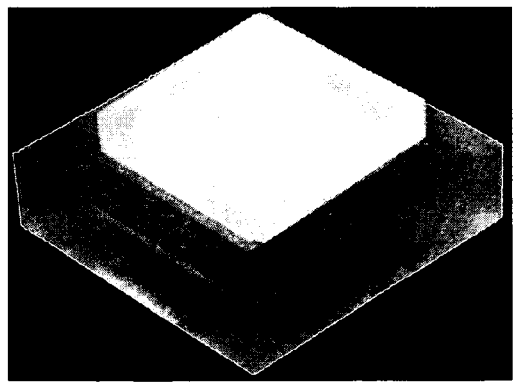
FIG. 5 is a diagram of examples of (a) the top and container part filled with the dental impression material; and (b) an impression of the dentitions in the container part after removal of the top part.
Figure 5:
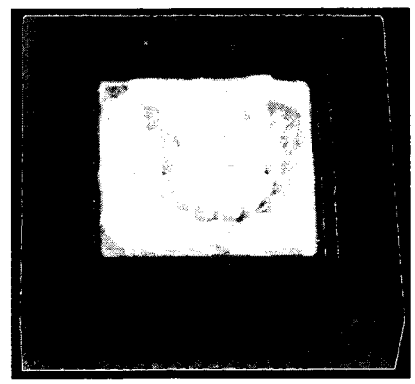

Certain embodiments of a specific design are as follows. As shown in FIG. 4, the designed object (10) may consist of two parts: a top part and a container part. The top part may be a cubic shaped block with at the lower side a structure which resembles the upper dentition. The container part may consist of two cavities. The size of the first cavity (C1 in FIG. 4b) can be slightly larger than the top part. The second cavity (C2 in FIG. 4b) can be slightly smaller than the top part. Due to the different sizes of the two cavities the top part can be placed on top of the container part in a well known position. To calibrate the impression material, the lower cavity C1 may be filled with the impression material (see FIG. 4b). Next the top part is placed on the container and the two parts are pushed into tight contact with each other. After a few minutes when the impression material has hardened, the top part can be removed. The remaining part, e.g., the container part with the impression material, defines the final calibration object which can be scanned to obtain the image volume of the calibration object (11). The dentition surface at the lower side of the top part can serve as the calibration object design (10).

Although the present inventions have been illustrated by reference to specific embodiments, it will be apparent to those skilled in the art that the inventions are not limited to the details of the foregoing illustrative embodiments, and that the present inventions may be embodied with various changes and modifications without departing from the scope thereof. The present embodiments are therefore to be considered in all respects as illustrative and not restrictive, the scope of the inventions being indicated by the appended claims rather than by the foregoing description, and all changes which come within the meaning and range of equivalency of the claims are therefore intended to be embraced therein. In other words, it is contemplated to cover any and all modifications, variations or equivalents that fall within the scope of the basic underlying principles and whose essential attributes are claimed in this patent application. It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfill the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

What is claimed is:

1. A method for capturing the shape of a dento-maxillofacial object out of volumetric image data of said dento-maxillofacial object, said method comprising:
   a. performing, via a computer, a segmentation of said volumetric image data with at least one calculated segmentation parameter indicative of a distinction between said dento-maxillofacial object and its background, and
   b. capturing, via the computer, the shape of said dento-maxillofacial object from said segmented volumetric image data.

2. The method of claim 1, wherein the segmentation is thresholding.

3. The method of claim 1, wherein the calculated segmentation parameter is based on a calibration object.

4. The method of claim 3, wherein the calculated segmentation parameter is based at least on volumetric image data of the calibration object.

5. A method for determining at least one segmentation parameter of volumetric image data of a dento-maxillofacial object, said method comprising:
   a. obtaining volumetric image data of a calibration object of a given shape with a same imaging protocol as used for obtaining said volumetric image data of said dento-maxillofacial object;
   b. aligning said volumetric image data of said calibration object with image data sets of said calibration object, c. deriving a measure for comparing said aligned data sets;

d. determining said at least one segmentation parameter using a selection criterion on said measure, whereby the shape of said calibration object and said volumetric image data of said calibration object are taken into account.

6. The method of claim 5, comprising computing an accuracy measure of a segmentation obtained by applying said at least one segmentation parameter.

7. The method of claim 5, wherein said aligning is performed by voxel-based registration or by a point based alignment method.

8. The method of claim 5 wherein said selection criterion is based on a histogram built by measuring image values in said volumetric image data of said calibration object at the surface of the aligned calibration object.

9. The method of claim 5 wherein said volumetric image data is obtained by a tomographic imaging technique comprising CT scanning.

10. The method of claim 5, wherein said calibration object has material properties substantially equal to those of said dento-maxillofacial object for said imaging protocol.

11. The method of claim 5, wherein said calibration object has a shape substantially equal to the shape of said dento-maxillofacial object.

12. The method of claim 5, wherein said calibration object has dimensions substantially equal to the dimensions of said dento-maxillofacial object.

13. A non-transitory computer readable medium comprising computer instructions of a program, executable on a programmable device containing the instructions, which when executed, perform the method as in claim 5.

14. A kit comprising a calibration object and the non-transitory computer readable medium containing the program of claim 13.

15. The kit of claim 14 further comprising an object for positioning said calibration object in an imaging device, said object imaging significantly different from said calibration object.

16. A method for digitizing a dento-maxillofacial object comprising:

a. taking a calibration object designed with material properties suitable for a tomographic imaging technique;

b. scanning the calibration object with a tomographic imaging device;

c. deriving at least one segmentation parameter;

d. scanning the dento-maxillofacial object with the same imaging device and settings as used for the calibration object in b;

e. applying a segmentation on the scanned dento-maxillofacial object with the at least one segmentation parameter obtained from c.

17. The method of claim 16, wherein said segmentation is thresholding.

18. The method of claim 16, wherein the calibration object is substantially equal to the dento-maxillofacial object in both shape and dimensions.

19. A non-transitory computer readable medium comprising computer instructions of a program, executable on a programmable device containing the instructions, which when executed, perform the method as in claim 16.

20. A kit comprising a calibration object and the non-transitory computer readable medium containing the program of claim 19.

21. The kit of claim 20 further comprising an object for positioning said calibration object in an imaging device, said object imaging significantly different from said calibration object.

22. The method of claim 16, wherein deriving of the at least one segmentation parameter is based on the calibration object.

23. The method of claim 22, wherein the deriving of the at least one segmentation parameter is based at least on volumetric image data from the scanning of the calibration object.

* * * * *